(12) United States Patent
Cibas

(10) Patent No.: US 6,468,208 B1
(45) Date of Patent: Oct. 22, 2002

(54) COMPUTER SYSTEM AND COMPUTER-IMPLEMENTED PROCESS FOR ANALYZING RESULTS OF CYTOLOGY TESTS FOR PERFORMANCE EVALUATION OF CYTOLOGISTS

(75) Inventor: Edmund S. Cibas, Boston, MA (US)

(73) Assignee: The Brigham & Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/318,871

(22) Filed: May 26, 1999

Related U.S. Application Data
(60) Provisional application No. 60/087,114, filed on May 29, 1998.

(51) Int. Cl.[7] .................................................. A61B 5/00
(52) U.S. Cl. ........................ 600/300; 600/301; 128/920; 128/923
(58) Field of Search ................................ 600/300, 301; 128/920–925

(56) References Cited

U.S. PATENT DOCUMENTS

| | | | | |
|---|---|---|---|---|
| 4,124,944 A | | 11/1978 | Blair | 434/234 |
| 5,257,182 A | | 10/1993 | Luck et al. | 382/224 |
| 5,463,548 A | * | 10/1995 | Asada et al. | 600/300 |
| 5,463,567 A | | 10/1995 | Boen et al. | 702/187 |
| 5,627,908 A | | 5/1997 | Lee et al | 382/133 |
| 5,677,966 A | | 10/1997 | Doerrer et al. | |
| 5,799,101 A | * | 8/1998 | Lee et al. | 382/133 |
| 5,839,438 A | | 11/1998 | Graettinger et al. | 600/300 |
| 5,889,880 A | | 3/1999 | Doerrer et al. | 382/128 |
| 6,327,377 B1 | * | 12/2001 | Rutenberg et al. | 382/133 |

OTHER PUBLICATIONS

Renshaw, et al. "Receiver Operating Characteristic Curves for Analysis of the Results of Cervicovaginal Smears", Arch Pathol Lab Med. Sep., 1997, 121: 968–975.*

Andrew A. Renshaw et al., "Receiver Operating Characteristic Curves for Analysis of the Resuls of the Results of Cervicovaginal Smears," Arch Pathol Lab Med. 1997; 121:968–975.

Paul Krieger et al., "Random Rescreening of Cytologic Smears: A Practical and Effective Component of Quality Assurance Programs in Both Large and Small Cytology Laboratories," Acta Cytologica, vol. 38, No. 3, 1994, pp. 291–298.

Fleiss, JL, *Statistical Methods for Rates and Proportions*, second edition (John Wiley, New York, 1988), pp. 212–236.

Aller, RD et al., "Computerized Reporting and Follow–Up of Gynecologic Cytology," Acta Cytol. 1991; 35:15–24.

Besley et al., *The Journal of the American Medical Association* ISSN:0098–7484 (pp. 775–786) (Feb. 14, 1986).

Graham, A.W., *Archives of Internal Medicine*, ISSN: 0003–9926 (151):958(7) (1991).

Mirami et al., *Chest.* ISSN:0012–3692 (vol. 105) (No. 6) p 1658(5) (Jun. 1994).

Zarbo, et al., *Archives of Pathology & Laboratory Medicine*, ISSN: 0363–0153, 115:743(8) (1991).

International Search Report—Int'l. Appl. No. PCT/US99/11477—filed May 25, 1999.

* cited by examiner

*Primary Examiner*—Robert L. Nasser
*Assistant Examiner*—Patricia Mallari
(74) *Attorney, Agent, or Firm*—Wolf, Greenfield & Sacks PC

(57) ABSTRACT

The evaluation of the performance of cytotechnologists and cytopathologists is obtained through statistical analyses of a computer system database including data representative of diagnosis by the cytotechnologists and cytopathologists. The statistical analyses provide objective measures of performance that aid in improving the quality of evaluation in the cytology laboratory. The locator skills, interpretive skills, volume statistics and productivity of the cytotechnologists is evaluated based on false-negative fraction information, divergent percentage calculations, average scores and kappa values, z scores and pro-rata workload measurements. The accuracy and performance of the cytopathologists is evaluated through the use of receiver operating characteristic curves and positive predictive values.

22 Claims, 6 Drawing Sheets

SEMIANNUAL CYTOTECHNOLOGIST
EVALUATION

Cytotechnologist: _____     Six-month Period: _____

| | CT | Laboratory | |
|---|---|---|---|
| LOCATOR SKILLS | | | |
| False-negative fraction 1 (ASCUS ⊕) | _____ | _____ | |
| False-negative fraction 2 (LSIL ⊕) | _____ | _____ | |
| | | | |
| INTERPRETIVE SKILLS (CT/CP DISREPANCY) | | | |
| % Discordant | _____ | _____ | |
| Average (weighted) score | _____ | _____ | |
| Kappa value | _____ | _____ | |
| | | | |
| VOLUME STATISTICS | | | Z-score |
| % UNSATISFACTORY | _____ | _____ | _____ |
| % ABNORMAL | _____ | _____ | _____ |
| | | | |
| PRODUCTIVITY | | | |
| Average slides/day | _____ | _____ | |
| Average hours/day | _____ | _____ | |
| Pro-rated workload | _____ | _____ | |

Prior slide limit: _____ slides/hr
New slide limit: _____ slides/hr

Prior workload target: _____ slides/hr
New workload target: _____ slides/hr

Comments: _____
_____
_____
_____

_____     _____
Technical Director      Date

_____     _____
Cytotechnologist        Date

*Fig. 1*

| | | | | |
|---|---|---|---|---|
| 12a | Case Identifier | | | |
| 12b | Patient Name | | | |
| 12c | Patient Information | | | |
| 12d | Cytotechnologist ID | | | |
| 12e | Cytopathologist ID | | | |
| slide # | Provisional Diagnosis | Time Stamp | Final Diagnosis | Biopsy Result |
| | | | | |
| | | | | |
| | | | | |
| | | | | |

(Block 10, group 12 with labels 13, 15, 19, 17, 21)

| | | | | |
|---|---|---|---|---|
| Case Identifier | | | | |
| Patient Name | | | | |
| Patient Information | | | | |
| Cyotechnologist ID | | | | |
| Cytopathologist ID | | | | |
| slide # | Provisional Diagnosis | Time Stamp | Final Diagnosis | Biopsy Result |
| | | | | |
| | | | | |
| | | | | |
| | | | | |

(Block 14)

Fig. 2

CT/CP DISCREPANCY

CYTOLOGY LAB

CP DIAGNOSIS

| CT DIAGNOSIS | UNS | WNL | BCC | EPM | ASCUS | AGUS | LSIL | SILUNC | HSIL | CAR |
|---|---|---|---|---|---|---|---|---|---|---|
| UNS | 17 | 2 | | | 1 | 3 | | | | |
| WNL | 1 | 19 | 34 | 2 | 30 | | 2 | | | |
| BCC | 47 | 25 | 1086 | 5 | 179 | 11 | 1 | | | |
| EPM | | 2 | | 23 | 1 | | | | | |
| ASCUS | 5 | 15 | 235 | | 1393 | 5 | 37 | 1 | 1 | |
| AGUS | 1 | 7 | 26 | 1 | 11 | 55 | | | | |
| LSIL | | | 1 | | 46 | | 300 | 11 | 8 | |
| SILUNC | | | | | 9 | | 4 | 70 | 3 | 1 |
| HSIL | | | | | 20 | 1 | 15 | 7 | 134 | |
| CAR | | | | | | | | | 3 | 7 |

NUMBER OF PAPS WITH CP: 3925
NUMBER CONCORDANT: 3104
NUMBER DISCORDANT: 821  20.92%
AVERAGE SCORE: 3.55
KAPPA: 0.69

COMPUTER SYSTEM AND COMPUTER-IMPLEMENTED PROCESS FOR ANALYZING RESULTS OF CYTOLOGY TESTS FOR PERFORMANCE EVALUATION OF CYTOLOGISTS

RELATED APPLICATIONS

The following application claims priority to provisional application serial no. 60/087,114, filed May 29, 1998 and entitled COMPUTER SYSTEM AND COMPUTER-IMPLEMENTED PROCESS FOR ANALYZING RESULTS OF CYTOLOGY TESTS FOR PERFORMANCE EVALUATION OF CYTOLOGISTS.

BACKGROUND

One function performed in cytology laboratories is the analysis of cervicovaginal smear (i.e., pap) slides to identify cell abnormalities. Each cytology laboratory may include a number of cytotechnologists, who perform an initial review of pap-smear slides to provide provisional diagnoses of the slides. The provisional diagnoses generally fall into the categories of unsatisfactory (i.e., the specimen on the slide was not substantial enough to accurately diagnose), normal/negative (i.e., the specimen included no abnormal cells) or abnormal/positive (i.e., the specimen included some number of abnormal cells).

Under federal law, cytotechnologists may release negative diagnoses, while cases having positive diagnoses are always reviewed by a senior cytopathologist. Because the negative diagnoses are not generally subject to a second review, there exists the risk that cases that actually showed an abnormality could be released as negative. Because this risk exists, the federal government requires that all cytology laboratories perform specific exercises in quality control to guarantee that the analyses are consistently accurate.

One method of maintaining quality control is through a slide audit, where a randomly selected set of slides, originally identified as negative, is re-screened to determine whether, in fact, the slides indicate positive findings of cell abnormality. Another method of maintaining quality control is to periodically perform performance evaluations of cytotechnologists. These performance evaluations have historically been performed by cytopathologists, and are generally subjective in nature. No consistent methods have been applied to evaluating the performance of the individual cytopathologists in the laboratory. It would be desirable to determine an improved method for providing performance evaluations of cytotechnologists and cytopathologists ("cytologists") in a cytology laboratory in order to improve the quality of evaluation of cervicovaginal smears.

SUMMARY

The evaluation of the performance of cytotechnologists and cytopathologists is obtained through statistical analyses of a computer system database including data representative of diagnosis by the cytotechnologists and cytopathologists. The statistical analyses provide objective measures of performance that aid in improving the quality of evaluation in the cytology laboratory.

Accordingly, in one aspect, a method for evaluating the performance of an individual in a cytology laboratory comprising the steps of collecting diagnosis data from at least one individual, comparing the diagnosis data from the at least one individual against an expected result to identify divergent diagnoses, statistically quantifying the divergence between the diagnosis data and the expected result and graphically displaying the statistical quantification of the divergence.

Accordingly, in another aspect, a method for evaluating the performance of a technologist comprising the steps of collecting provisional diagnosis data from at least one technologist for a plurality of cases, selecting a set of the plurality of cases for re-screening, the re-screening providing final diagnosis data and comparing the final diagnosis data to the provisional diagnosis data to generate statistical evaluation information quantifying locator skills and interpretive skills of the at least one technologist.

According to another aspect, a computer system for evaluating performance of technologists includes a processor capable of performing the steps of collecting provisional diagnosis data from at least one technologist for a plurality of cases, selecting a set of the plurality of cases for re-screening, the re-screening providing final diagnosis data and comparing the final diagnosis data to the provisional diagnosis data to generate statistical evaluation information quantifying locator skills and interpretive skills of the at least one technologist.

According to another aspect, a computer system for evaluating the accuracy of cytological diagnoses comprises means for periodically receiving and storing evaluation data for a plurality of cases of cytology slides, the evaluation data including, for each of the plurality of cases, an identifier of an individual that evaluated the case, at least one diagnosis of at least one slide associated with the case, and a time stamp indicating when the respective case was diagnosed, means for generating statistical evaluation information quantifying the locator skills and interpretive skills of each of a plurality of individuals, using the evaluation data.

DESCRIPTION OF THE FIGURES

FIG. 1 is one embodiment of a form that may be used for performance evaluations of cytotechnologists in a cytology laboratory;

FIG. 2 is one embodiment of a database that may be used by a computer system to generate data for the form of FIG. 1 using statistical analyses according to one embodiment of the invention;

FIG. 3 illustrates one embodiment of a table relating cytotechnologist diagnoses to cytopathologist diagnoses for providing indicia of performance of a cytotechnologist in one embodiment of the invention;

DETAILED DESCRIPTION

Figure 4:
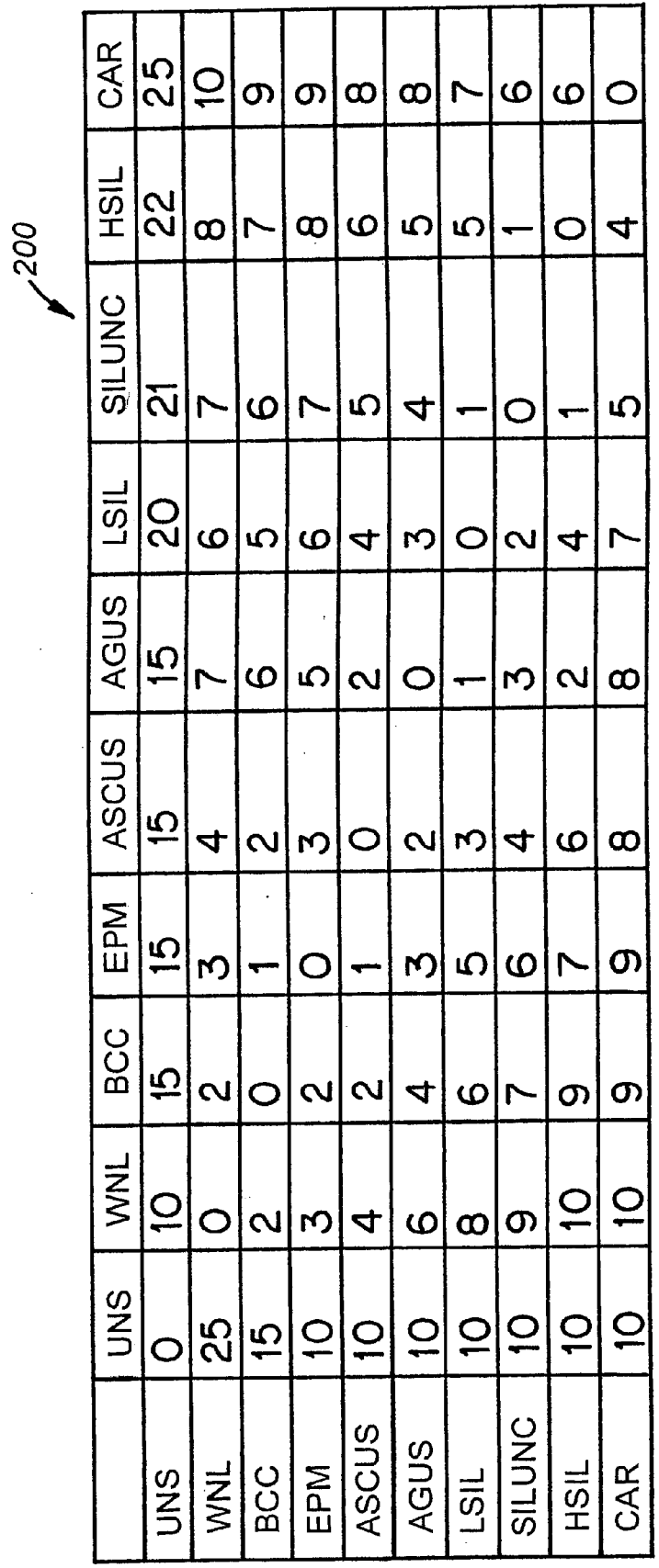
FIG. 4 illustrates one embodiment of a table including weightings that may be applied to the table of FIG. 3 for determining an average performance of a cytotechnologist.

The following detailed description should be read in conjunction with the attached drawing in which similar reference numbers indicate similar structures. All references cited herein are hereby expressly incorporated by reference.

As mentioned above, under current federal laws, periodic performance evaluations of cytotechnologists must be performed to ensure that high quality, consistent diagnoses are maintained in cytology laboratories. A method for evaluating the performance of cytotechnologists is introduced that uses a computer system to statistically analyze individual diagnosis information for each cytotechnologist to provide objective measures of the skill and productivity levels of the cytotechnologist. Analysis of the performance evaluations for each of the cytotechnologist enables a manager of the cytotechnologists to manage the work flow of the cytotechnologists to improve the accuracy of the diagnoses in the laboratory.

An example of some objective measures that may be included in a performance evaluation are summarized in a "semi-annual cytotechnologist evaluation" form shown in FIG. 1. This form provides a suitable format for a computer display. As shown in FIG. 1, the performance evaluation examines the locator skills, interpretive skills, volume statistics and productivity of the individual cytotechnologist, and compares the individual results against the laboratory as a whole. According to one embodiment of the invention, the evaluation information to be provided in the form of FIG. 1 for each cytotechnologist is obtained by the computer system using statistical methods to analyze a relational database of the laboratory.

In order to understand how the statistical methods are applied to obtain performance results, a general overview of the contents of the relational database will first be described with regard to FIG. 2. An example relational database 10 is shown to include a number of case records, such as case records 12 and 14. (Although only two case records are shown, it is understood that there may be thousands of case records in the relational database). Each case record includes a case identifier 12a, a patient identifier 12b, patient information 12c, a cytotechnologist identifier 12d and a cytopathologist identifier 12e. Other information may also be included and the present invention is not limited to any particular types of information being stored in the database 10.

In addition, each case record includes diagnostic information for one or more slides associated with the case. Thus, the case record also includes, for each slide, a slide number 13, a provisional diagnosis field 15, a time stamp 19, a final diagnosis, field 17 and a biopsy field 21. The provisional diagnosis is the diagnosis of the slide as determined by the cytotechnologist indicated in the cytotechnologist identifier field 12d. The final diagnosis is the diagnosis of the slide as determined by a cytopathologist indicated by the cytopathologist identifier 12e. The timestamp is an indication of when the cytotechnologist entered the diagnosis into the case record. The biopsy field 21 includes the diagnosis of the slide after biopsy, and is used to confirm the diagnosis by the cytopathologist and for evaluation of the performance of the cytopathologist as described in more detail below.

In one embodiment, the diagnoses available to the cytotechnologist fall into the ten basic categories. These categories include: unsatisfactory (UNS), within normal limits (WNL), benign cellular changes (BCC), endometrial cells cytologically benign in a post menopausal woman (EPM), atypical squamous cells of undetermined significance (ASCUS), atypical glandular cells of undetermined significance (AGUS), low-grade squamous intraepithilial lesion (LSIL), squamous intraepithelial lesion, difficult to grade (SLIUNC), high-grade squamous intraepithelial lesion (HSIL) and carcinoma (CAR). The ten basic categories can be grouped into unsatisfactory, normal (i.e., negative) and abnormal (i.e., positive) categories. In one embodiment, the unsatisfactory category encompasses the UNS diagnosis. The normal/negative category includes the WNL and BCC diagnoses. The abnormal/positive group includes all other diagnoses.

According to typical cytology laboratory practices, any diagnosis which falls into one of the abnormal categories is always verified by a cytopathologist in the laboratory. As described above, under federal laws a cytotechnologist is able to release negative diagnoses but quality control methods are implemented to monitor the number of false-negatives that are released by a cytotechnologist and/or laboratory. Using the false-negative information, the cytopathologist may change practices within the laboratory (such as the number of slides analyzed by the cytotechnologist per hour) in order to minimize the false-accuracy information.

One method of monitoring the number of false-negatives is to have a cytologist re-screen a set of cases diagnosed by the cytotechnologist as negative. The cases that are selected for re-screening comprise a combination of randomly selected cases and cases from patients that have a history of abnormalities. The patient information field 12c of the case record is used to identify cases where the patient has a history of abnormalities. A "cytologist" as used herein includes cytotechnologists and cytopathologists.

The cytologist re-screens the set of cases to provide a final diagnosis. The final diagnosis may be compared against the provisional diagnosis provided by the original cytotechnologist to identify diagnostic errors. The diagnostic errors may be used to provide objective indications of the locator skills, interpretive skills, volume statistics and productivity of each of the cytotechnologists. How the data in the relational database 10 is interpreted to provide these performance indicia is described in more detail below.

Locator Skills

The locator skills reflect the ability of the cytotechnologist to identify atypical and/or abnormal cells in a screening. Another cytologist re-screens the slides evaluated by a cytotechnologist to identify false negatives. False negatives include those slides which were diagnosed as negative but, upon later examination by the cytopathologist were diagnosed to be positive or unsatisfactory. The number of false negatives provides a false negative factor (FNF). The FNF is thus an indication of the number of diagnostic errors in the laboratory.

To determine what constitutes a false negative, it must first be determined the threshold or degree of cell abnormality that should require a positive diagnosis. For example, the threshold of abnormality could be low, where any atypical slide should trigger a positive diagnosis by the cytotechnologist . Alternatively, the threshold could be higher, where potentially cancerous slides are those that should trigger a positive finding, and lesser, atypical slides should not necessarily indicate a positive result.

One method of using a FNF to evaluate performance in a cytology laboratory is described in "Random Re-screening of Cytologic Smears: A practical and Effective Component of Quality Assurance Programs in Both Large and Small Cytology Laboratories", ACTA Cytologica, volume 38, number 3, pp. 291–297, May-June 1994, by Krieger et al., incorporated herein by reference.

In Krieger et al, the threshold for false negatives is set at the lowest, atypical cell threshold. Using such a threshold, Krieger calculates the false-negative fraction (FNF) using the below Equation I:

$$\text{FNF} = \text{\# false-negatives}/(\text{true-positives} + \text{false-negatives}) \quad \text{Equation I:}$$

The FNF of Krieger is determined using only randomly selected case samples.

In contrast, according to one embodiment of the invention, two different FNFs (FNF1 and FNF2) are calculated to evaluate the locator skills of each cytotechnologists. The calculation of the two different FNFs takes into account that the cases include a combination of historically generated quality control cases (i.e., from women with a history of pap smear abnormalities) and a randomly selected quality control cases. FNF1 sets the threshold for a false-negative at relatively low diagnosis of atypical squamous cells of undetermined significance (ASCUS) while FNF2 sets the threshold for a false-negative at a relatively higher low grade squamous intraepithelial lesion (LSIL). Thus, FNF1 is a lower threshold than FNF2. Both FNF1 and FNF2 provide meaningful information as to the performance of the cytotechnologist. FNF1 will typically provide more data for the individual, while FNF2 provides more reproducible results. Equation II below provides one formula that may be used to obtain FNF1, while Equation III below provides one formula that may be used to obtain FNF2.

$$FNF1 = \frac{hqcr + (rqcr*((totn - hqc)/rqc))}{(eca + uns + hqcr) + (rqcr*((totn - hqc)/rqc))}$$

$$FNF2 = \frac{(hqcr - haty) + ((rqcr - raty)*((totn - hqc)/rqc))}{(eca - taty) + (uns) + (hqcr - haty) + ((rqcr - raty)*((totn - hqc)/rqc))}$$

where:
- hqc=# of history generated quality control cases (i.e., cases for women with a history of abnormalities)
- rqc=# of randomly selected quality control cases
- hqcr=# hqc cases reclassified
- rqcr=# rqc cases reclassified
- haty=# hqc cases reclassified as atypical
- raty=# rqc cases reclassified as atypical
- taty=# cases with primary diagnostic category of atypical
- eca=# cases with general category of abnormal
- uns=# of cases of category unsatisfactory
- totn=#normal cases The data used to calculate FNF1 and FNF2 for each of the cytotechnologists is obtained from the database in the following manner. As described above, a subset of the cases are selected for re-screening, with the subset including cases selected randomly and cases selected for historical reasons. The subset of cases selected for re-screening are reviewed by another cytologist and a final diagnosis is placed in the database associated with each case. To evaluate the performance of an individual cytotechnologist, the subset of re-screened cases is searched by cytotechnologist identifier to obtain a set of all of the cases that were analyzed by the individual cytotechnologist. This sub-set is hereinafter referred to as the re-screened subset.

The re-screened subset of cases is then analyzed to determine which of the cases has had their diagnosis reclassified. The number of the re-classified cases provides the rrqc value. Total values for the haty, raty, taty, eca, uns and totn variables may be obtained by analyzing the provisional and final diagnosis fields of each case and increasing the variable according to the number of cases having the associated diagnosis. These totals are used to generate the FNFs for the particular cytotechnologist, and are inserted in Form 1. In general, it is desirable for each FNF to be below twenty percent to indicate adequate performance by the cytotechnologist, and in another embodiment below 15° percent. It is conceivable that these thresholds may vary from lab to lab.

Interpretive Skills

The interpretive skills of the cytotechnologist may be objectively measured using a statistical comparison of the provisional diagnoses of the cytotechnologist and the final diagnosis provided by the cytopathologist. Three criteria are provided to identify the interpretive skills of the cytotechnologist including a discordant percentage, an average score and a Kappa value. The discordant percentage indicates the percent of time that there is a disagreement between the cytotechnologist and the cytopathologist. The average score indicates a level of disagreement between the cytotechnologist and the cytopathologist. The Kappa value is an unweighted measure of the degree of concordance between observers which ranges from 0–1.0.

In one embodiment, the values for the discordant percentage, average score and Kappa value may be obtained through the generation of a cytotechnologist (CT)/cytopathologist (CP) discrepancy table such as table 100 shown in FIG. 3. A separate row (column) is provided for each of the ten possible diagnosis by the cytotechnologist (cytopathologist). The diagnoses increase in degree of cell abnormality from UNS to CAR. Other diagnoses could also be provided and the present invention is not limited to any particular set of diagnoses.

Each entry in the table 100 includes a count of how many cases that the cytopathologist diagnosed as having the diagnosis indicated by the associated column of the entry, and that the cytotechnologist diagnosed as having the diagnosis indicated by the associated row of the entry. For example, at column one, row two, one case diagnosed by the cytopathologist as unsatisfactory (UNS) was diagnosed as WNL by the cytotechnologist.

The sum of the values in each column of the discrepancy table indicates the number of diagnosis decisions of the particular type (such as unsatisfactory, for example) made by the cytopathologist, while the sum of each row of the discrepancy table indicates the number of diagnosis decisions of the particular type made by the cytotechnologist. Thus, in the example of FIG. 2, the cytopathologist diagnosed seventy-one cases as unsatisfactory, while the cytotechnologist diagnosed twenty-four cases as unsatisfactory. In only seventeen cases did the diagnosis decisions of the two match for this diagnostic category. The diagonal of the table, from upper left hand corner to lower right hand corner, (with the numbers illustrated in bolded text) represent concordant diagnoses of the cytotechnologist and the cytopathologist. The other entries in the table 100 represent discordant diagnoses.

Using the discrepancy table, the percentage of discordant diagnoses may be determined according to below Equation IV:

$$\% \text{ Discordant} = \frac{\text{Number discordant}}{\text{Number of Cases Reviewed by a Cytopathologist}}$$

In general, a discordant percentage of less than twenty percent is desirable. The average weighted score is obtained by collecting each of the discordant cases, (i.e., those cases in which the cytotechnologist and cytopathologist disagreed), and assigning a value to the level of disagreement. The higher the value, the higher the degree of error in the diagnosis of by the cytotechnologist. An example of weighted values that may be applied to each of the entries of the table in FIG. 3 is shown in FIG. 4. The diagnoses which fall close to the diagonal (representing concordant diagnoses) are assigned a relatively lower weighted value, with the weighted values increasing as the diagnoses increase in distance from the diagonal. Unsatisfactory diagnoses are highly weighted to maximize the error attributed to those cases which are diagnosed as normal by a cytotechnologist but which, in fact, represent an unsatisfactory specimen.

To calculate the average score for a cytotechnologist, the number of diagnoses in each of the entries of the table of FIG. 3 is multiplied by the weighted value in the corresponding entry of table 200 of FIG. 4. The resulting values of each entry in the table 100 are summed and the total is divided by the total number of cases evaluated in the given time period. A higher average score therefore indicates a higher level of discordance of the particular cytotechnologist. In the evaluation sheet of FIG. 1, comparing the average score of an individual cytotechnologist against the laboratory average may provide an objective measurement of the degree of discordance between that individuals' diagnosis as compared to the laboratory on the whole. In general, an average score less than five is desirable.

Figure 5:
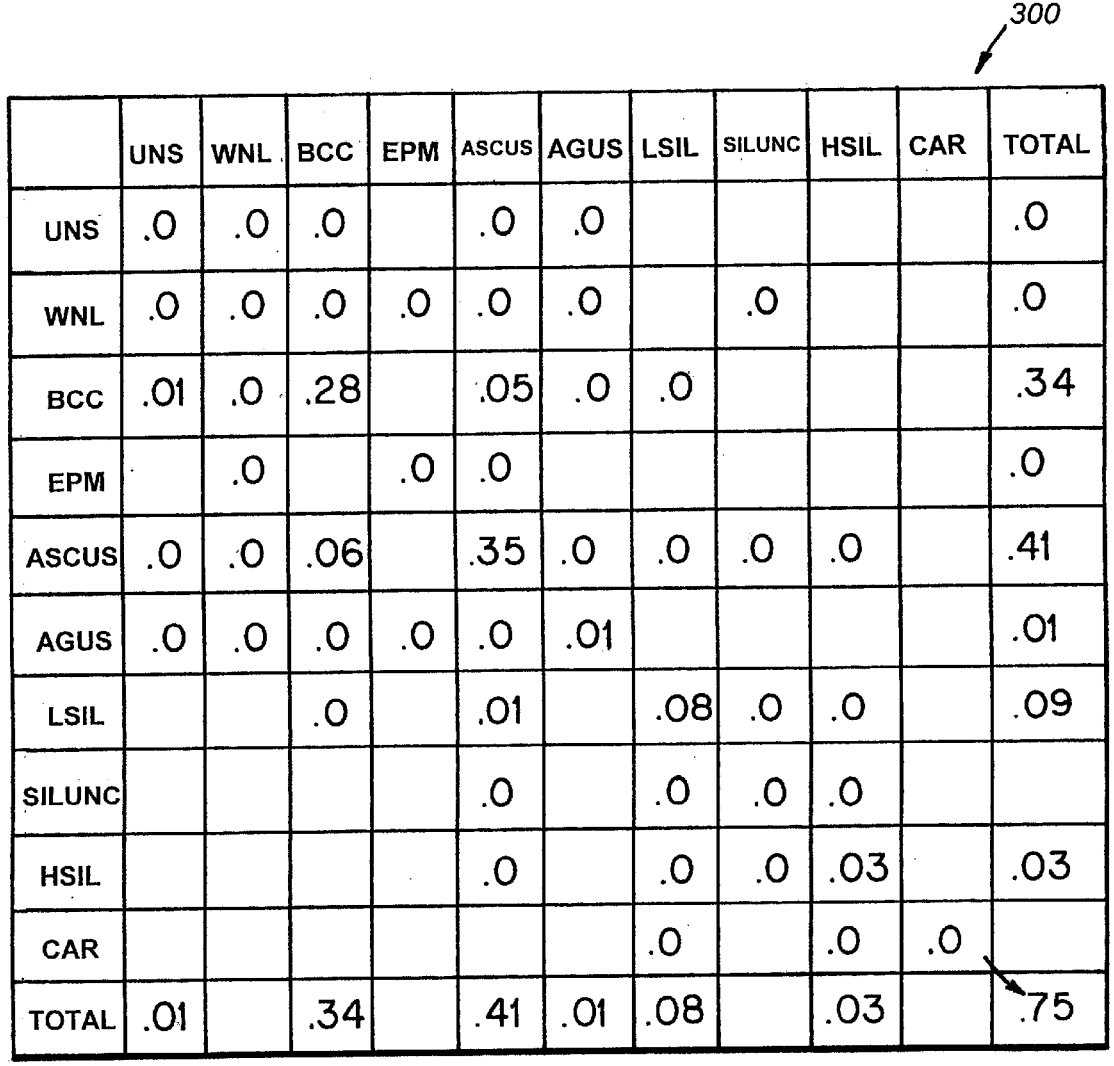
FIG. 5 illustrates one embodiment of the table in FIG. 3, with each entry in the table of FIG. 3 being translated into a frequency component for use in evaluating the concurrence of the diagnoses of the cytotechnologist with diagnosis by the cytopathologist.

As mentioned above, the Kappa ($\kappa$) value is an unweighted measure of the degree of concordance between two observers (the cytotechnologist and the cytopathologist) which ranges from 0–1. A $\kappa$ value of 1 indicates complete agreement. If observed agreement is less than or equal to chance agreement, $\kappa <= 0$. If observed agreement is greater than or equal to chance agreement $\kappa => 0$. A detailed description of the use and generation of the $\kappa$ is described in "Statistical Methods", by Fliess, chapter 13, pp. 212–236, incorporated herein by reference. One method of determining a $\kappa$ value for use in evaluating performance of cytotechnologists in a cytology laboratory translates the diagnosis values of FIG. 2 into frequency values by dividing each entry in the table 100 by the total number of diagnoses in the table. The translation of the diagnosis values into frequency values is shown as table 300 in FIG. 5.

Once the diagnosis values have been translated to frequency values, the $\kappa$ value may be determined according to below Equation IV:

$$\kappa = \frac{Po - Pe}{1 - Pe}$$

Where Po is the sum of the frequency values in the diagonal that represents the concordance between the cytopathologist and cytotechnologist, and Pe is equal to (Cptot$_{col}$ $_1$ * Cttot$_{row}$ $_1$)+(Cptot$_{col}$ $_2$+Cttot$_{row}$ $_2$) . . . (Cptot$_{col}$ $_n$+Cttot$_{row}$ $_n$), where n=maximum number of diagnoses. In general, a $\kappa$ value of greater than 0.75 is excellent, between 0.6 and 0.75 is good, between 0.4 and 0.6 is fair, and less than 0.4 is poor.

Volume Statistics

Volume statistics measure the percentage of cases that a cytotechnologist called unsatisfactory and abnormal. These percentages are determined according to Equations V and VI below:

$$\% \text{ Unsatisfactory} = \frac{\text{Number Unsatisfactory}}{\text{Total Diagnosed}}$$

$$\% \text{ Abnormal} = \frac{\text{Number } EPM, ASCUS, AGUS, LSIL, HSIL, SILUNC, CAR}{\text{Total Diagnosed}}$$

wherein EPM indicates endometrial cells, cytologically benign in a postmenopausal woman; ASCUS indicates atypical squamous cells of undetermined significance; AGUS indicates atypical glandular cells of undetermined significance; LSIL indicates low grade squamous intraepithelial lesion; HSIL indicates high grade squamous intraepithelial lesion; SILUNC indicates squamous intraepithelial lesion unclassifiable (difficult to grade); and CAR indicates invasive carcinoma. Thus, each of the percentages is calculated by summing up the total number of slides reviewed by the cytotechnologist that were diagnosed as unsatisfactory and abnormal, (using data from the case record in the relational database) and dividing each of these numbers by the total number of slides reviewed during the time period. This measurement gives an indication of the number of slides that were reviewed by the cytotechnologist which require subsequent analysis. The percentages of unsatisfactory and abnormal are compared with the laboratory average to determine whether or not the performance of the cytotechnologist is in conformance with the overall laboratory.

In one embodiment, the variance from the laboratory average is measured statistically using the "Z score." The z score can be determined using below Equation VII:

$$z = \frac{x - \mu}{\sigma}$$

where x is the value of observation (i.e., the percentage of the unsatisfactory or abnormal diagnoses by the cytotechnologist), t is the mean of the distribution of unsatisfactory or abnormal diagnoses across the entire laboratory, and a is the standard deviation of the distribution. A Z score greater than 2.0 or less than −2.0 shows a difference from the laboratory average by greater than or less than two standard deviations, and is generally undesirable.

Productivity

The productivity measurement identifies average number of slides that the cytotechnologist evaluates per hour in a given time period. The productivity measurement for each cytotechnologist may be determined by searching for the cytotechnologist identifier 12d in the database 10, and retrieving all of the cases having a timestamp within the given time period. Using this data, a value called the "pro-rated workload" is calculated using the below Equation VIII.

$$\text{Pro-rated Workload} = \frac{\text{Average Number slides per day}}{\text{Average number of hours per day}}$$

According to federal laws, a cytotechnologist is limited to reviewing 100 slides per day, or 12.5 slides per hour. Using the locator skill, interpretive skills, volume statistics and productivity statistics, the cytopathologist managing the cytology lab may reduce the number of slides that each individual cytologist is to review in order to increase the accuracy of the individual's diagnoses. Thus, the performance evaluation technique uses statistical analysis to provide feedback that can be used to increase the overall quality of diagnoses by the cytology laboratory.

The present invention is not limited to the statistical methods shown above or to any particular type of diagnosis. Rather, whatever data is valuable to measuring the performance of the individual cytologists may also be included without diverging from the scope of the present invention.

In addition, the concept of utilizing statistical analysis data to analyze performance of individuals in a cytology laboratory may be extended to analyzing the performance of cytopathologists. Historically, the quality of the diagnoses by cytopathologists was monitored based on the ratio of cases reported as atypical squamous cells of undetermined significance (ASCUS) to those interpreted as squamous intraepithelial lesion (SIL). While the absolute rate of these diagnoses varied considerably between laboratories, the ratio between the two was relatively consistent. Thus, the ASCUS/SIL ratio provides a good measure for judging the performance of cytopathologists in the laboratories. Guidelines indicate that the ASCUS/SIL ratio of a laboratory, and by implication of an individual cytopathologist, should be maintained at less than 3 or even less than 1 to indicate accurate diagnoses.

However, while the ASCUS/SIL ratios provide useful quality assessment, they may not reflect the variations in diagnoses by the individual cytopathologists. For example, this ratio would not reflect different diagnostic thresholds for negative diagnosis by the individual pathologists, nor would it reflect diagnostic accuracy.

According to one embodiment of the invention, the evaluation of the performance of a cytopathologist is evaluated using two statistical measures; a receiver operating characteristic curve (ROC) and a positive predictive value (PPV). Receiver operating characteristic curves graphically display the true-positive rate (sensitivity) versus the false-positive rate (1-specificity) for a particular test. Thus, the ROC may be used to distinguish a difference in diagnostic thresholds and in diagnostic accuracy. Diagnostic threshold differences may be discerned by comparing different points of the ROC at different places along the ROC curve. The diagnostic accuracy may be determined by comparing separate ROC curves against an expected standard. Diagnoses having greater accuracy have an ROC curve that is shifted upward and the left, resulting in a larger area under the curve than one with less accuracy. Accordingly, the greater the diagnostic accuracy, the greater the area under the ROC curve.

The PPV may be used to quantify the accuracy of the diagnoses by the cytopathologist. In order to provide a comparative evaluation of the performance of a cytopathologist using either an ROC or a PPV, a control must be provided. The control is the accurate result to which the diagnosis of the cytopathologist is compared in order to determine whether, in fact, the cytopathologist has made an error in diagnosis. In one embodiment, the control is a biopsy which was performed for each of the cases. A biopsy is not necessarily performed for each case; accordingly, in one embodiment, the cases that are selected for evaluating the performance of a cytopathologist include only those cases in which a corresponding biopsy was later performed. Thus, to select a set of cases for evaluation, the database 10 is searched by cytopathologist identifier (field 12*e*, FIG. 2) to identify those cases that have a result in the biopsy field 21. The selected set of cases forms an evaluation database for evaluating the performance of the cytopathologist.

It should be understood that the present invention is not limited to the control being a biopsy. Rather, any method for verifying the diagnosis of the sample, for example, a re-screen by a second cytopathologist, could alternatively be used.

A threshold is selected for determining which diagnoses constitute a positive diagnosis (i.e., indicate a high enough presence of abnormal cells to constitute a positive diagnosis by the cytopathologist). In one embodiment, only biopsies diagnostic of LSIL, HSIL, or squamous cell carcinoma (CAR) were considered positive; all other biopsies, including those suspicious for but not diagnostic of SIL, were considered negative. Both sensitivity and specificity are calculated based on the selected thresholds for those cases in which a control diagnosis is available. The present invention is not limited to the selection of any particular threshold.

Figure 6:
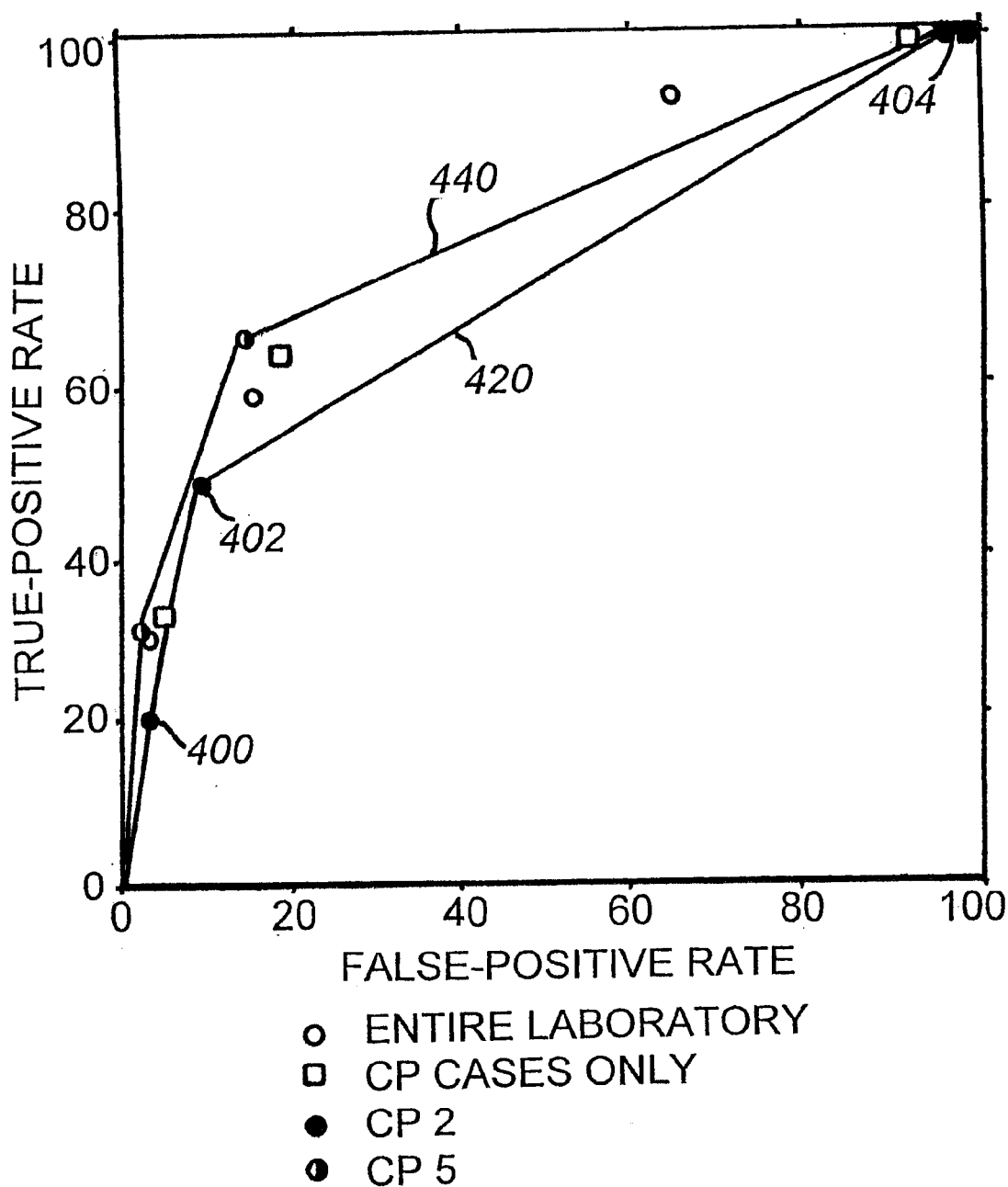
FIG. 6 is a receiver operating characteristic curve having a true positive rate (sensitivity) plotted on the Y axis and a false positive rate (1-sensitivity) plotted on the x axis to identify differences in diagnostic thresholds by cytopathologists.

An example of an ROC curve is illustrated in FIG. 6. The intercepts of 100% sensitivity and 0% specificity, and 0% sensitivity and 100% specificity are fixed, since by diagnosing all smears as either positive or negative, one would obtain these results. The true-positive rate (sensitivity) may be plotted along the Y axis, and the false-positive rate (1-specificity) may be plotted along the X axis. In one embodiment, a true-positive result is considered any biopsy with a diagnosis of either LSIL, HSIL, or squamous cell carcinoma.

Three free points along the curve, (400, 402 and 404) each define a different diagnostic threshold. The first point 400 represents all smears interpreting ASCUS, LSIL, or HSIL as a positive test result. The second point 402 represents all smears interpreting either LSIL or HSIL (but not ASCUS) as a positive test result. The last point 404 represents only smears interpreting HSIL as a positive test result. In one embodiment, for comparison purposes, point 404 represents only biopsy results with a diagnostic HSIL or squamous cell carcinoma as a true positive result.

Thus, the resulting ROC was composed of two fixed intercepts and three free points. The three free points correspond to the thresholds for each diagnostic category. Thus, the locations of each of these points on the ROC may be used to identify differences in diagnostic thresholds by cytopathologists in the laboratories.

As mentioned above, the area under the ROC curves may be used to evaluate the accuracy of diagnoses by the individual cytopathologists. The differences in accuracy between the cytopathologists may be obtained by comparing the areas under the two ROC curves of different cytopathologists. Alternatively, the accuracy may be assigned a Z score, by comparing the ROC curve generated using data from a cytopathologist, against an expected ROC curve reflecting expected accuracy and garnered from historical ROC data. The Z score could be calculated using Equation VII above.

Accordingly, a statistical method of evaluating the performance of cytopathologists uses data from the relational database including the final diagnosis of a cytopathologist and corresponding biopsy results to provide a statistical quantification of the divergence between the diagnosis of the cytopathologist and the true diagnosis of the sample. By using such a method, the cytopathologist may be able to quantify their performance and alter their practice (i.e., by altering the thresholds, etc.) in order to more closely conform with an expected accuracy.

In addition to the ROC curve, the performance of the cytopathologist may be quantified using a positive predictive value (PPV). The PPV represents the total accuracy of the predictions of the cytopathologist. The PPV may be calculated using the below equation IX:

$$PPV = \frac{\text{Number True Positives}}{\text{Number True Positives} + \text{Number False Positives}}$$

The PPV may therefore be used to 'score' the performance of the cytopathologist to compare their performance against a laboratory average.

As mentioned above, the performance evaluation methods may be implemented in a computer system. A computer system for implementing this system as a computer program typically includes a main unit connected to both an output device which displays information to a user and an input device which receives input from a user. The main unit generally includes a processor connected to a memory system via an interconnection mechanism. The input device and output device also are connected to the processor and memory system via the interconnection mechanism.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, and data input devices such as sensors. It should be understood the invention is not limited to the particular input or output devices used in combination with the computer system or to those described herein.

The computer system may be a general purpose computer system which is programmable using a computer programming language, such as FORTRAN, "C++," Visual Basic, JAVA or other language, such as a scripting language or even assembly language. The computer system may also be specially programmed, special purpose hardware. In a general purpose computer system, the processor is typically a commercially available processor, of which the series x86 and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which WindowsNT, UNIX, DOS, VMS and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the invention is not limited thereto. It should also be understood that the invention is not limited to a particular memory system.

It should be understood the invention is not limited to a particular computer platform, particular processor, or particular high-level programming language. Additionally, the computer system may be a multiprocessor computer system or may include multiple computers connected over a computer network. It should be understood that each formula and related data input and output may be separate modules of a computer program, or may be separate computer programs. Such modules may be operable on separate computers.

Having now described a few embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention.

What is claimed is:

1. A method for evaluating the performance of an individual in a cytology laboratory comprising steps of:

collecting a plurality of diagnoses from at least one individual;

comparing the plurality of diagnoses from the at least one individual against a plurality of expected diagnoses to identify divergent diagnoses;

statistically quantifying the divergence between the plurality of diagnoses and the plurality of expected diagnoses, wherein statistically quantifying the divergence includes the step of generating statistical evaluation information quantifying locator skills and interpretive skills of the individual; and graphically displaying the statistical quantification of the divergence.

2. The method according to claim 1, wherein the evaluation information further quantifies productivity and volume statistics of the individual.

3. The method according to claim 1, wherein the step of statistically quantifying the divergence includes the step of graphically displaying a true-positive diagnosis rate against a false-negative diagnosis rate to provide a receiver operating characteristic (ROC) curve for the at least one individual.

4. A method for evaluating the performance of an individual in a cytology laboratory comprising steps of:

collecting a plurality of diagnoses from at least one individual;

comparing the plurality of diagnoses from the at least one individual against a plurality of expected diagnoses to identify divergent diagnoses;

statistically quantifying the divergence between the plurality of diagnoses and the plurality of expected diagnoses, wherein statistically quantifying the divergence includes the step of generating a positive predictive value (PPV) for the individual using the below equation:

$$PPV = \frac{\text{Number True Positives}}{\text{Number True Positives} + \text{Number False Positives}}$$

wherein the Number True Positives corresponds to a number of the plurality of diagnoses that indicate a positive diagnosis and match a corresponding one of the plurality of expected diagnoses, and wherein the Number False Positives corresponds to the number of the plurality of diagnoses that indicate a positive diagnosis and do not match a corresponding one of the plurality of expected diagnoses; and graphically displaying the statistical quantification of the divergence.

5. The method according to claim 4, wherein the step of statistically quantifying the divergence includes the step of graphically displaying a true-positive diagnosis rate against a false-negative diagnosis rate to provide a receiver operating characteristic (ROC) curve for the at least one individual.

6. A method for evaluating the performance of a technologist comprising the steps of:

collecting provisional diagnosis data from at least one technologist for a plurality of cases;

selecting a set of the plurality of cases for re-screening by at least one cytologist, the re-screening providing final diagnosis data; and comparing the final diagnosis data to the provisional diagnosis data to generate statistical evaluation information quantifying locator skills and interpretive skills of the at least one technologist.

7. The method according to claim 6, wherein the statistical evaluation information further includes statistical information quantifying the productivity and volume of the at least one technologist.

8. The method according to claim 6, wherein the information quantifying the locator skills of the at least one technologist includes false-negative fraction information indicating a number of cases in the set of cases selected for re-screening having a provisional diagnosis differing from the final diagnosis, and wherein the step of comparing further comprises the step of generating a false-negative fraction to represent the performance of the at least one technologist.

9. The method according to claim 8, wherein the set of the plurality of cases comprises a first number of cases of a first type and a second number of cases of a second type, and wherein the step of generating a false-negative fraction (FNF1) is determined according to the below equation:

$$FNF1 = \frac{hqcr + (rqcr * ((totn - hqc)/rqc))}{(eca + uns + hqcr) + (rqcr * ((totn - hqc)/rqc))}$$

wherein:

hqc=the first number of the first type of cases rqc=the second number of the second type of cases hqcr=a number of the first type of cases wherein the provisional diagnosis differs from the final diagnosis rqcr=a number of the second type of cases wherein the provisional diagnosis differs from the final diagnosis haty=a number of the first type of cases having a final diagnosis of atypical raty=a number of the second type of cases having a final diagnosis of atypical taty=a total number of the set of cases having a provisional diagnosis of atypical eca=a total number of the set of cases having a final diagnosis of abnormal uns=a total number of the set of cases having a final diagnosis of unsatisfactory totn=a total number of the set of cases having a final diagnosis of normal.

10. The method according to claim 8. wherein the set of the plurality of cases comprises a first number of cases of a first type and a second number of cases of a second type, and wherein the step of generating the false-negative fraction (FNF2) uses the below equation:

$$FNF2 = \frac{(hqcr - haty) + ((rqcr - raty) * ((totn - hqc)/rqc))}{(eca - taty) + (uns) + (hqcr - haty) + ((rqcr - raty) * ((totn - hqc)/rqc))}$$

hqc=the first number of the first type of cases rqc=the second number of the second type of cases hqcr=a number of the first type of cases wherein the provisional diagnosis differs from the final diagnosis rqcr=a number of the second type of cases wherein the provisional diagnosis differs from the final diagnosis haty=a number of the first type of cases having a final diagnosis of atypical raty=a number of the second type of cases having a final diagnosis of atypical taty=a total number of the set of cases having a provisional diagnosis of atypical eca=a total number of the set of cases having a final diagnosis of abnormal uns=a total number of the set of cases having a final diagnosis of unsatisfactory totn=a total number of the set of cases having a final diagnosis of normal.

11. The method according to claim 6, wherein the information quantifying the interpretive skills of the technologist includes a discordant percentage, and wherein the step of comparing further includes a step of generating the discordant percentage using the below equation:

$$\% \text{ Discordant} = \frac{\text{Number discordant}}{\text{Number of the plurality of cases}}$$

12. The method according to claim 6, wherein the information quantifying the interpretive skills of the technologist includes an average score, and wherein the step of comparing further includes a step of generating the average store, the step of generating including the steps of:

storing, in an array comprising a plurality of entries arranged in a plurality of rows and a corresponding plurality of columns, each row and column associated with one of a plurality of types of diagnoses, a number of each of the provisional and final diagnoses of the types indicated by the row and column;

applying a weighted value to each of the plurality of entries to provide a plurality of weighted entries, the weighted value corresponding to a degree of error between the provisional and final diagnoses associated with the types indicated by the row and column; and summing the weighted entries to provide the average score.

13. The method according to claim 6, wherein the information quantifying the interpretive skills of the technologist includes a kappa ($\kappa$) value, and wherein the step of comparing further includes a step of generating the kappa value, the step of generating including the steps of:

storing, in an array comprising a plurality of entries arranged in a plurality of rows and a corresponding plurality of columns, each row and column associated with one of a plurality of types of diagnoses, a frequency of the provisional and final diagnoses of the types indicated by the row and column; and generating the κ value according to the below equation, where n corresponds to a number of the plurality of types of diagnoses:

$$\kappa = \frac{Po - Pe}{1 - Pe}$$

where:

$$Po = \sum_{i=0, j=0}^{i=n, j=n} Array(i, j)$$

$$Pe = \sum_{i=0}^{i=n} \left(\sum Array(Row_i) \times \sum Array(Column_i)\right).$$

14. The method according to claim 6, wherein the information quantifying the volume statistics of the technologist includes a first percentage of the plurality of diagnoses having an unsatisfactory diagnosis and a second percentage of the plurality of diagnoses having an abnormal diagnosis.

15. The method according to claim 14, wherein the information quantifying the volume statistics of the technologist includes a first z score, relating the first percentage of the technologist to a percentage of a first type of diagnoses in the laboratory, and a second z score relating the second percentage to a percentage of a second type of diagnoses in the laboratory, and wherein the respective first and second z scores are determined according to the below equation:

$$z = \frac{x - \mu}{\sigma}$$

where x is a value of respective first or second percentage, $\mu$ is a mean of the distribution of the diagnoses of the respective first or second type, and $\sigma$ is a standard deviation of the distribution of the diagnoses of the respective first or second type.

16. A computer system for evaluating performance of technologists including a processor capable of performing the steps of:

collecting provisional diagnosis data from at least one technologist for a plurality of cases;

selecting a set of the plurality of cases for re-screening, the re-screening providing final diagnosis data; and comparing the final diagnosis data to the provisional diagnosis data to generate statistical evaluation information quantifying locator skills and interpretive skills of the at least one technologist.

17. The computer system according to claim 16, wherein the information quantifying the locator skills of the at least one technologist includes false-negative fraction information indicating a number of cases in the set of cases selected for re-screening having a provisional diagnosis differing from the final diagnosis.

18. The computer system according to claim 17, wherein the set of the plurality of cases comprises a first number of cases of a first type and a second number of cases of a second type, and wherein the false-negative fraction (FNF2) information is determined according to the below equation:

$$FNF2 = \frac{(hqcr - haty) + ((rqcr - raty) * ((totn - hqc)/rqc))}{(eca - taty) + (uns) + (hqcr - haty) + ((rqcr - raty) * ((totn - hqc)/rqc))}$$

hqc=the first number of the first type of cases rqc=the second number of the second type of cases hqcr=a number of the first type of cases wherein the provisional diagnosis differs from the final diagnosis rqcr=a number of the second type of cases wherein the provisional diagnosis differs from the final diagnosis haty=a number of the first type of cases having a final diagnosis of atypical raty=a number of the second type of cases having a final diagnosis of atypical taty=a total number of the set of cases having a provisional diagnosis of atypical eca=a total number of the set of cases having a final diagnosis of abnormal uns=a total number of the set of cases having a final diagnosis of unsatisfactory totn=a total number of the set of cases having a final diagnosis of normal.

19. The computer system according to claim 17, wherein the set of the plurality of cases comprises a first number of cases of a first type and a second number of cases of a second type, and wherein the false-negative fraction (FNF1) information is determined according to the below equation:

$$FNF1 = \frac{hqcr + (rqcr * ((totn - hqc)/rqc))}{(eca + uns + hqcr) + (rqcr * ((totn - hqc)/rqc))}$$

wherein:

hqc=the first number of the first type of cases rqc=the second number of the second type of cases hqcr=a number of the first type of cases wherein the provisional diagnosis differs from the final diagnosis rqcr=a number of the second type of cases wherein the provisional diagnosis differs from the final diagnosis haty=a number of the first type of cases having a final diagnosis of atypical raty=a number of the second type of cases having a final diagnosis of atypical taty=a total number of the set of cases having a provisional diagnosis of atypical eca=a total number of the set of cases having a final diagnosis of abnormal uns=a total number of the set of cases having a final diagnosis of unsatisfactory totn=a total number of the set of cases having a final diagnosis of normal.

20. The computer system according to claim 16, wherein the statistical evaluation information further includes statistical information quantifying the productivity and volume of the at least one technologist.

21. The computer system according to claim 20 further comprising a graphical user interface for displaying the statistical evaluation information for the at least one technologist.

22. A computer system for evaluating the accuracy of cytological diagnoses comprises:

means for periodically receiving and storing evaluation data for a plurality of cases of cytology slides, the evaluation data including, for each of the plurality of cases, an identifier of an individual that evaluated the case, at least one diagnosis of at least one slide associated with the case, and a time stamp indicating when the respective case was diagnosed;

means for generating statistical evaluation information quantifying the locator skills and interpretive skills of each of a plurality of individuals, using the evaluation data.

* * * * *